(12) United States Patent
Crainich et al.

(10) Patent No.: US 9,433,422 B2
(45) Date of Patent: Sep. 6, 2016

(54) SURGICAL CLIP APPLICATOR (71) Applicant: DESIGN STANDARDS CORPORATION, Charlestown, NH (US)

(72) Inventors: Lawrence Crainich, Charlestown, NH (US); Joseph Trabka, Charlestown, NH (US); Maurice Gilchrest, Charlestown, NH (US); Thomas Carignan, Charlestown, NH (US)

(73) Assignee: Design Standards Corporation, Charlestown, NH (US)

( * ) Notice: Subject to any disclaimer, the term of this patent is extended or adjusted under 35 U.S.C. 154(b) by 302 days.

(21) Appl. No.: 14/226,763

(22) Filed: Mar. 26, 2014

(65) Prior Publication Data

US 2014/0324074 A1   Oct. 30, 2014

Related U.S. Application Data

(60) Provisional application No. 61/805,511, filed on Mar. 26, 2013.

(51) Int. Cl.
*A61B 17/128* (2006.01)

(52) U.S. Cl.
CPC .................. *A61B 17/1285* (2013.01)

(58) Field of Classification Search
CPC ............ A61B 17/122; A61B 17/1222; A61B 17/1227; A61B 17/128; A61B 17/1285; A61B 2017/1225
See application file for complete search history.

(56) References Cited

U.S. PATENT DOCUMENTS

| | | | | | |
|---|---|---|---|---|---|
| 4,296,751 | A | * | 10/1981 | Blake, III | A61B 17/128 227/145 |
| 4,372,316 | A | * | 2/1983 | Blake, III | A61B 17/128 206/339 |
| 4,427,008 | A | * | 1/1984 | Transue | A61B 17/128 227/117 |
| 4,509,518 | A | * | 4/1985 | McGarry | A61B 17/128 606/143 |
| 4,556,058 | A | * | 12/1985 | Green | A61B 17/128 29/243.56 |
| 4,611,595 | A | * | 9/1986 | Klieman | A61B 17/128 606/143 |
| 4,674,504 | A | * | 6/1987 | Klieman | A61B 17/128 606/143 |
| 5,112,343 | A | * | 5/1992 | Thornton | A61B 17/1285 606/142 |
| 5,171,247 | A | * | 12/1992 | Hughett | A61B 17/1285 606/142 |
| 5,354,304 | A | * | 10/1994 | Allen | A61B 17/122 227/901 |

(Continued)

*Primary Examiner* — Ryan J Severson
(74) *Attorney, Agent, or Firm* — Bachman & LaPointe, PC (57) ABSTRACT

A surgical clip applicator includes a handle configured to produce translational movement; a cartridge containing a plurality of clips arranged in a row, the cartridge including a jaw assembly for receiving and closing a clip; a jaw closing mechanism for closing the jaw assembly; a clip feed mechanism for serially feeding a lead clip from the row to the jaw assembly; a clip advance mechanism for advancing the row as the lead clip is fed to the jaws; and a rocker mechanism for translating translational movement from the handle opposite translational movement of the haw closing mechanism in one direction and the clip feed mechanism and clip advance mechanism in an opposite direction.

10 Claims, 9 Drawing Sheets

(56) References Cited

U.S. PATENT DOCUMENTS

| | | | | |
|---|---|---|---|---|
| 5,395,381 | A * | 3/1995 | Green | F16B 2/22 227/19 |
| 5,431,668 | A * | 7/1995 | Burbank, III | A61B 17/128 227/901 |
| 5,637,108 | A * | 6/1997 | Vidal | A61B 17/1285 606/1 |
| 5,976,160 | A * | 11/1999 | Crainich | A61B 17/2909 606/142 |
| 6,099,537 | A * | 8/2000 | Sugai | A61B 17/0684 606/143 |
| 6,277,131 | B1 * | 8/2001 | Kalikow | A61B 17/1285 227/19 |
| 6,520,972 | B2 * | 2/2003 | Peters | A61B 17/1285 606/142 |
| 6,599,298 | B1 * | 7/2003 | Forster | A61B 17/128 606/139 |
| 7,052,504 | B2 * | 5/2006 | Hughett | A61B 17/1285 606/139 |
| 7,179,265 | B2 * | 2/2007 | Manetakis | A61B 17/1285 606/142 |
| 7,211,092 | B2 * | 5/2007 | Hughett | A61B 17/068 606/142 |
| 7,585,304 | B2 * | 9/2009 | Hughett | A61B 17/10 606/142 |
| 8,403,946 | B2 * | 3/2013 | Whitfield | A61B 17/1285 227/901 |
| 8,585,718 | B2 * | 11/2013 | Disch | A61B 17/1222 606/143 |
| 8,968,337 | B2 * | 3/2015 | Whitfield | A61B 17/1285 606/142 |
| 2001/0047178 | A1 * | 11/2001 | Peters | A61B 17/1285 606/139 |
| 2004/0010272 | A1 * | 1/2004 | Manetakis | A61B 17/1285 606/143 |
| 2004/0097970 | A1 * | 5/2004 | Hughett | A61B 17/1285 606/142 |
| 2004/0097971 | A1 * | 5/2004 | Hughett | A61B 17/068 606/142 |
| 2005/0171560 | A1 * | 8/2005 | Hughett | A61B 17/10 606/142 |
| 2010/0274264 | A1 * | 10/2010 | Schulz | A61B 17/1285 606/143 |
| 2012/0029533 | A1 * | 2/2012 | Whitfield | A61B 17/1285 606/143 |
| 2012/0029534 | A1 * | 2/2012 | Whitfield | A61B 17/1285 606/143 |
| 2012/0048759 | A1 * | 3/2012 | Disch | A61B 17/1285 206/339 |
| 2013/0165951 | A1 * | 6/2013 | Blake, III | A61B 17/1285 606/143 |
| 2013/0165952 | A1 * | 6/2013 | Whitfield | A61B 17/1285 606/143 |
| 2014/0324074 | A1 * | 10/2014 | Crainich | A61B 17/1285 606/143 |
| 2015/0127022 | A1 * | 5/2015 | Whitfield | A61B 17/1285 606/143 |
| 2015/0164511 | A1 * | 6/2015 | Whitfield | A61B 17/1285 606/143 |

* cited by examiner

FIG. 13
FIG. 14 DETAIL C
FIG. 15 DETAIL D
FIG. 16
FIG. 17 DETAIL E

SURGICAL CLIP APPLICATOR

CROSS REFERENCE TO RELATED APPLICATION

This application is a non-provisional application of U.S. application Ser. No. 61/805,511, filed Mar. 26, 2013, which is incorporated herein by reference in its entirety.

BACKGROUND OF THE INVENTION

The invention relates generally to devices that apply surgical or ligating clips. More specifically, the invention relates to a device that rapidly deploys clips at a surgical site.

There are many different designs for surgical clip applicators for a variety of surgical procedures. Several types of surgical clips are known for ligating vessels and ducts. One type of surgical clip employs a generally U-shaped configuration. However, a kink forms in the bend of such a clip during closing, and the position of the kink must be carefully controlled to maintain the relative position and closure of the legs. Otherwise, the U-shaped clip may have gaps when closed, allowing leakage, or may become V-shaped and allow vessel slippage.

The U-shaped clip is intended to reduce slippage of the vessel out of the open end of the clip. However, slippage of the vessel remains a problem. To eliminate vessel slippage out of U-shaped clips, serrations or indentations have been formed on the inside of the legs for gripping and holding the vessel after closure of the clip. However, even with such structures, it is often required to apply two or more clips to the vessel to assure closure of the vessel and retention.

What is desired is a surgical clip applicator that allows for a rapid and reliable deployment of clips.

SUMMARY OF THE INVENTION

The inventors have discovered that it would be desirable to have a repeating clip applier having a simplified mechanism for applying clips. The clip applicator is suitable for various clips and for applying such clips in different types of procedures including laparoscopy, or minimally invasive surgery (MIS), as well as for open procedure ligation.

One aspect of the invention is a two-piece surgical clip applicator. Applicators according to this aspect are two-piece in that they have a disposable cartridge and a universal handle. These components form a delivery system for the application of surgical clips. The applicator is a semi-automatic device for applying clips one at a time around a vessel or tissue. An operating lever on the handle is squeezed to apply a clip, and a pawl within the handle prevents re-opening of the handle until a full stroke is complete. This prohibits the clip from loosening until the clip is fully compressed. During operation of the applicator, a closer component within the cartridge moves in a forward direction as a transfer lever moves in a rearward direction. A linear, reciprocating motion with respect to the cartridge is achieved for the closer component and transfer lever for each cycle of the operating lever. A clip pusher at the end of the transfer lever descends below the plane of a clip magazine as a ramp of the clip pusher makes contact with a clip shelf slot end. At the maximum travel of the handle lever, the clip is fully compressed around the vessel or tissue and the handle resets and allows the jaws to relax along with the lever. As the lever retracts, a reciprocating operation loads another clip into the applicator jaws as soon as they are fully open.

The invention provides that the clip applicator can be made as a disposable cartridge to be inserted into a disposable or non-disposable handle with the cartridge removed from the handle and discarded after its clips are consumed. The simplified mechanism reduces tooling and assembly requirements, and provides high operating reliability at lower product cost.

According to the invention, a surgical clip applicator is provided which comprises a handle configured to produce translational movement; a cartridge containing a plurality of clips arranged in a row, the cartridge comprising; a jaw assembly for receiving and closing a clip; a jaw closing mechanism for closing the jaw assembly; a clip feed mechanism for serially feeding a lead clip from the row to the jaw assembly; a clip advance mechanism for advancing the row as the lead clip is fed to the jaws; and a rocker mechanism for translating translational movement from the handle to opposite translational movement of the jaw closing mechanism in one direction and the clip feed mechanism and clip advance mechanism in an opposite direction.

Each of the mechanisms interacts with the rocker mechanism which is entirely mechanical in nature and therefore more predictable and reliable. This allows the applicator according to the invention to conveniently and reliably apply clips as desired, with reduced or avoided issues concerning dropped or misapplied clips. The cartridge can be reused or discarded, and the handle can be re-used with successive cartridges as needed.

The details of one or more embodiments of the invention are set forth in the accompanying drawings and the description below. Other features, objects, and advantages of the invention will be apparent from the description and drawings.

BRIEF DESCRIPTION OF THE DRAWINGS

A detailed description of embodiments of the invention follows, with reference to the attached drawings, wherein.

DETAILED DESCRIPTION

Embodiments of the invention will be described with reference to the accompanying drawing figures wherein like numbers represent like elements throughout. Before embodiments of the invention are explained in detail, it is to be understood that the invention is not limited in its application to the details of the examples set forth in the following description or illustrated in the figures. The invention is capable of other embodiments and of being practiced or carried out in a variety of applications and in various ways. Also, it is to be understood that the phraseology and terminology used herein is for the purpose of description and should not be regarded as limiting. The use of "including," "comprising," or "having," and variations thereof herein is meant to encompass the items listed thereafter and equivalents thereof as well as additional items. The terms "mounted," "connected," and "coupled," are used broadly and encompass both direct and indirect mounting, connecting, and coupling. Further, "connected," and "coupled" are not restricted to physical or mechanical connections or couplings.

Figure 1:
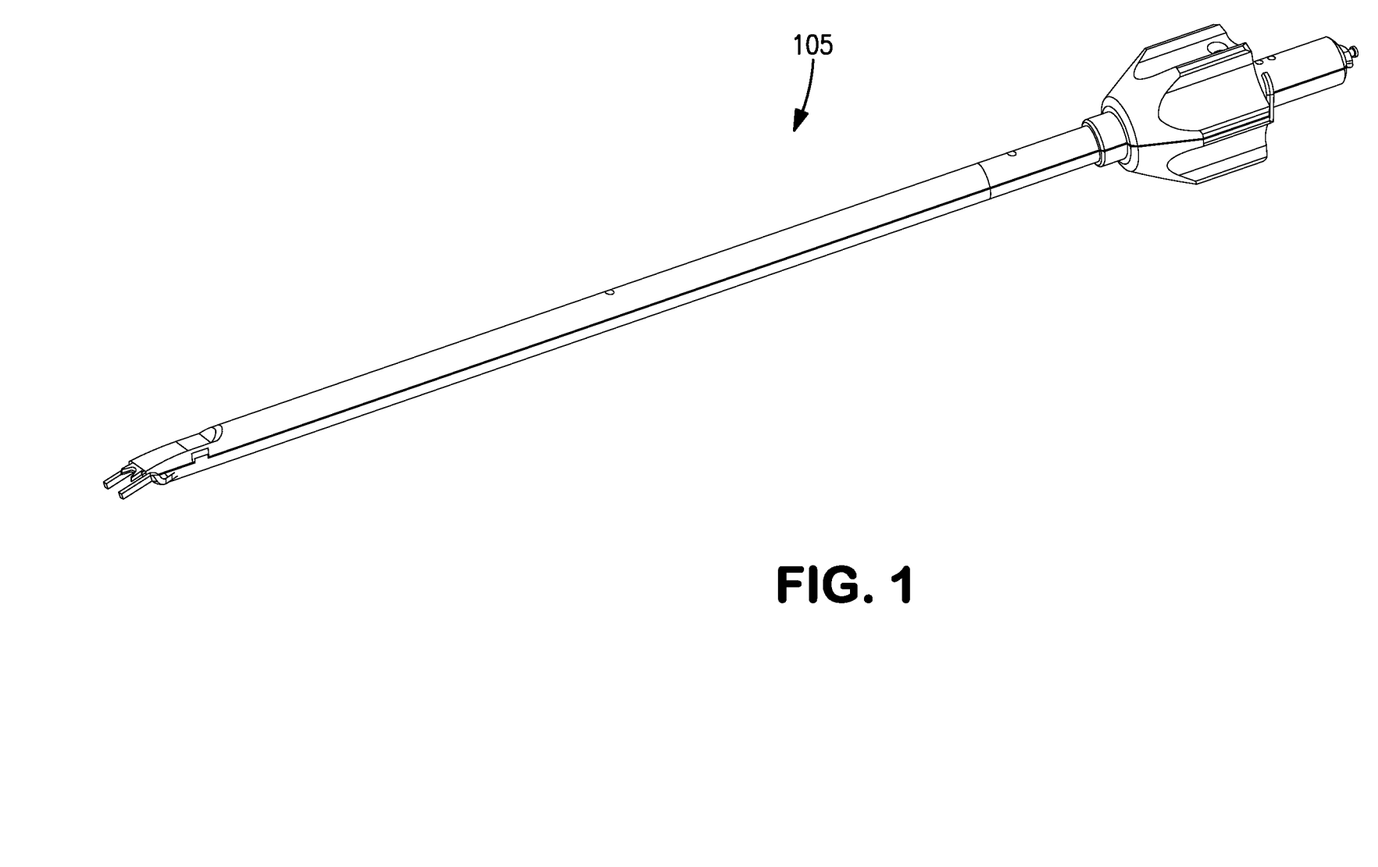
FIG. 1 is a perspective view of a cartridge of an exemplary two-piece disposable cartridge/universal handle surgical clip applicator.
Figure 2:
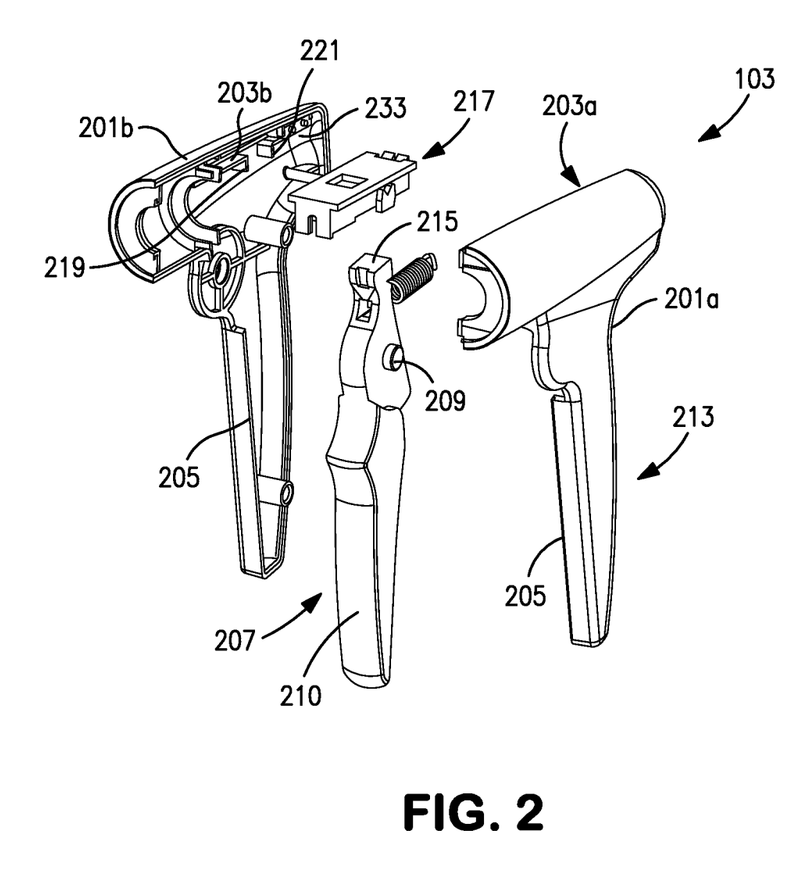
FIG. 2 is an exemplary exploded perspective view of a universal handle for the cartridge of FIG. 1.

FIG. 1 shows a cartridge 105 of a two-piece surgical clip applicator according to the invention. FIG. 2 shows a universal handle 103 for use with removable cartridge 105. The exchangeable cartridge allows for different lengths (short or long reach) and different surgical clip sizes (allowable diameters, for example) as well as replenishing the clip supply as necessary. This also permits loading cartridges containing different amounts of clips.

FIG. 2 shows an exploded view of universal handle 103. This handle is considered to be universal because it is designed for use with various different cartridges 105 such as cartridges for skin staplers, linear staplers, cutters and the like. The handle 103 can include a body formed of left and right shells 201a, 201b which can be substantially mirror images of each other, each of which can have aligned confronting journal guide slots 203a, 203b. The shells 201a, 201b are joined to each other along edges 205 to define an enclosure for receiving an operating lever 207 pivotally mounted on pins 209 that are captured by both body shells.

Figure 4:
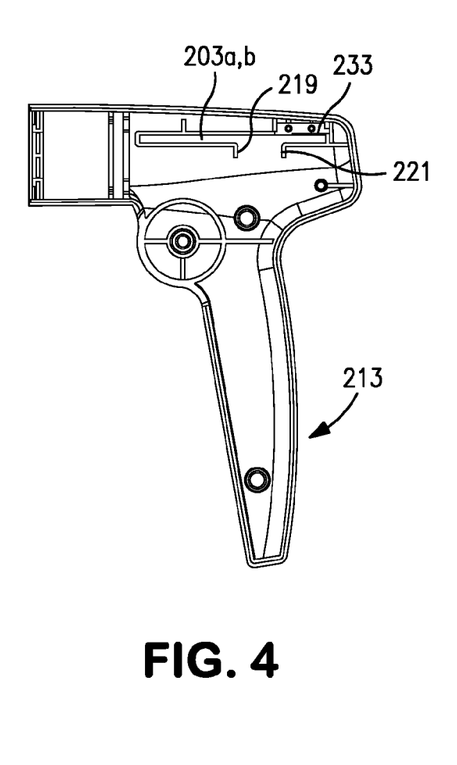
FIG. 4 is an exemplary internal elevation view of the universal handle right body shell.

The operating lever 207 can include a surface 210 for applying force from the fingers of a hand or a finger loop, for a user to place one or more fingers through. The user's thumb and/or palm provide a secure purchase around a body grip 213. The surface 210 is for exerting an input force on one end of the lever 207, and a rocker 215 exerts a corresponding output force. The rocker 215 communicates with a sliding carriage assembly 217 guided in guide slots 203a, 203b (also shown in FIG. 4). The motion imparted by pivot of lever 207 results in carriage assembly 217 moving in a limited, linear excursion along guide slots 203a, 203b. The extent of this linear excursion is defined by front and rear guide stops. In use, lever 207 is squeezed against grip 213 to compress a surgical clip previously dispensed from a clip magazine of cartridge 105. After a clip is compressed, a stored spring force within cartridge 105 moves lever 207 away from grip 213 to reload jaws of cartridge 105 with a new, uncompressed clip. Operating lever 207, pins 209 and rocker 215 act as a first-class lever, effectively multiplying the input force.

Carriage assembly 217 is comprised of a body 223 (see also FIG. 3) having a front actuating surface 225 and guide rails 227a, 227b, a pawl spring 229 and a rotary cam 231. The rotary cam 231 includes an internal cam 232 which controls the pawl spring 229 and two mirror image external cams 234a, 234b residing on either side of the carriage body 223 that set and reset the internal cam 232 when they come in contact with the rear and front guide stops 221, 219, respectively. Internal cam 232 and two external cams 234a, 234b can be coupled together on a common shaft. Depending on the location of carriage assembly 217 in guide slots 203a, 203b, rotary cam 231 assumes two different positions that affect engagement of pawl spring 229 on a rack 233 located within the body shells (also shown in FIGS. 4-6).

Figure 3:
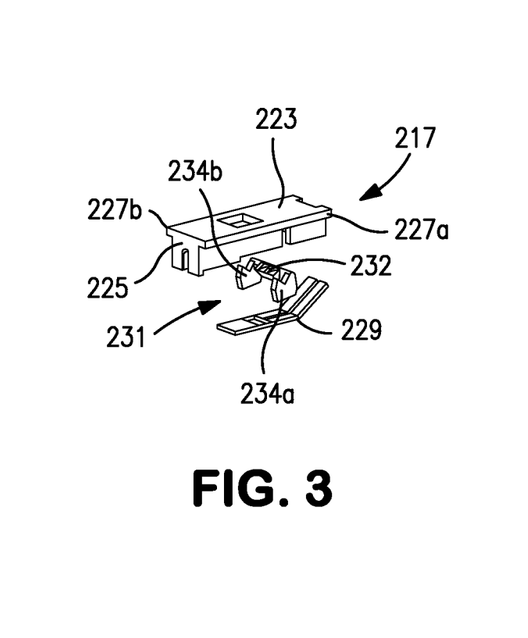
FIG. 3 is an exploded view of a subassembly of the handle of FIG. 2.

FIG. 3 shows an enlarged view of carriage assembly 217 and related components. These components function as described in prior U.S. Pat. No. 5,344,061 to Crainich, which is incorporated herein by reference. Components of assembly 217 serve to engage pawl spring 229 with a rack 233 in cartridge 109 during a closing stroke of the handle, and to disengage pawl spring 229 upon completion of the closing stroke. Disengaging of pawl spring 229 allows the handle to return to an open position, at which time pawl spring 229 is again engaged with rack 233, which prevents opening of trigger 211 until a closing stroke is again completed.

Figure 5:
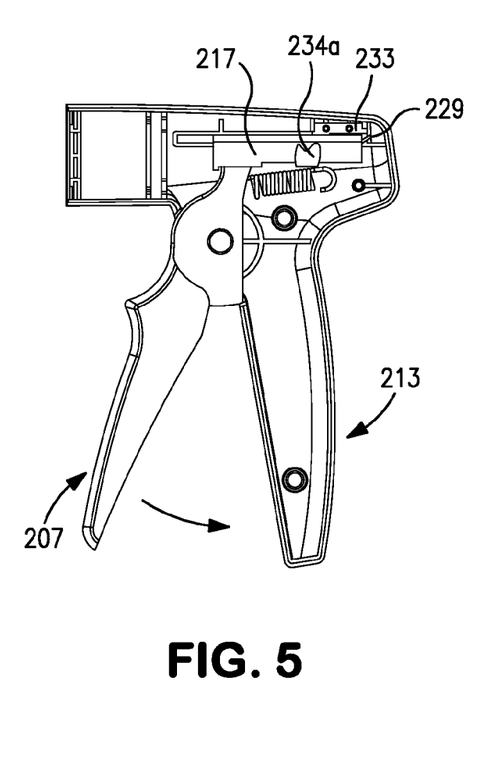
FIG. 5 is an exemplary internal elevation view of the universal handle right body shell.

FIG. 5 shows the first, or engaged position where pawl spring 229 ratchets against rack 233. The engaged position only allows operating lever 207 to travel in one direction, toward the body grip 213 as shown by the arrow in FIG. 5. Rotary cam 231 is rotated by contact with rear guide stops 221 into an engaged position wherein pawl spring 229 is in position to engage rack 233, and this corresponds to a fully open position of the handles.

In a preferred configuration, pawl spring 229 can be a split pawl having separate pawls on arms of different length. This allows for alternating engagement of one pawl and then the other pawl, thereby providing finer control over closing movement.

Figure 6:
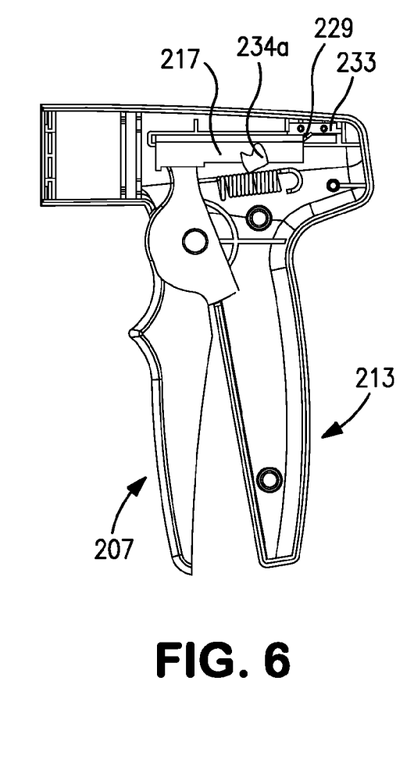
FIG. 6 is an exemplary internal elevation view of FIG. 5 with the operating lever fully depressed.

FIG. 6 shows the second, or disengaged position where pawl spring 229 is held away from rack 233 by rotation of rotary cam 231. When lever 207 is fully depressed, rotary cam 231 contacts front guide stops 219 causing the cam to rotate and move pawl spring 229 away from rack 233, thereby disengaging pawl spring 229 from rack 233. This allows the handles to return to an open position in preparation for application of the next clip.

A further aspect of the invention is a reliable quick release mechanism between handle 103 and cartridge 105. This structure is also described in prior U.S. Pat. Nos. 5,407,293 and 5,464,360 to Crainich, incorporated herein by reference.

Figure 7:
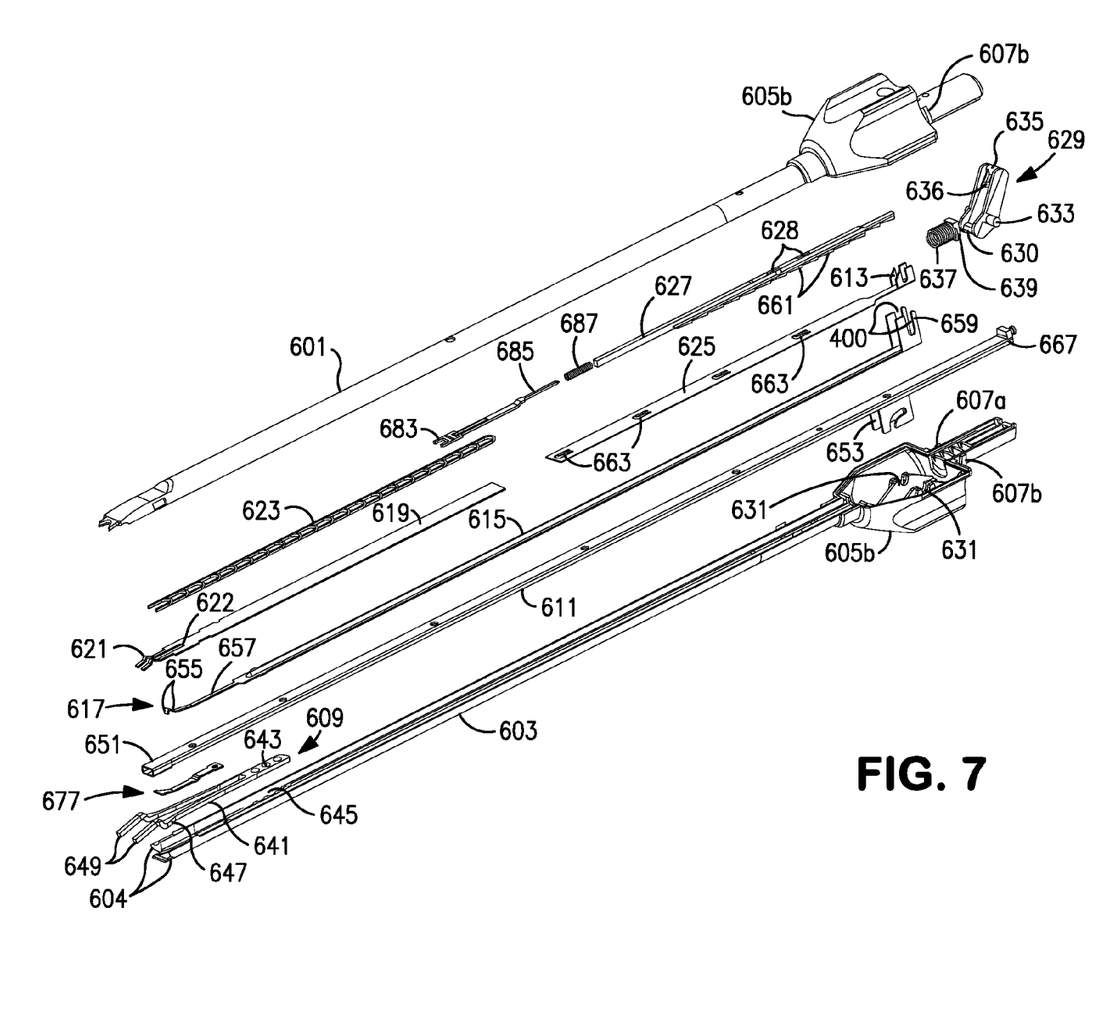
FIG. 7 is an exemplary exploded perspective view of the cartridge shown in FIG. 1.

FIG. 7 shows an exploded view of cartridge 105 according to the invention. Cartridge 105 has a cartridge housing that includes a cover 601 and a base 603. The cartridge housing defines an elongate open ended channel and can have a large preferably fluted coupling end surface 605a, 605b to aid a user's grip when exchanging a cartridge from handle 103. This also provides a grip for rotation of the cartridge relative to the handle. The coupling includes two quick release blades 607a, 607b that correspond with the configuration of the quick release mechanism discussed above, such that blades 607a, 607b may be aligned with quick release tabs and, inserted into the handle body.

In the description that follows, cartridge cover 601 and base 603 are regarded as stationary in relation to movement of the internal clip applier mechanism components. The internal components are assembled together in layers and are at least partially slidable relative to housing base 603.

Base 603 has two internal shelves defining two planes for supporting further internal components and two jaw opening stops 604. The applier mechanism components may include a clip applicator fork 609 and a closer component 611 slidably disposed on the first shelf. A transfer lever 615 including a clip pusher 617 can be slidably disposed on the closer 611. A clip shelf 619 with clip stops 621 for supporting and guiding a predetermined number of surgical clips 623 can be positioned above a portion of lever 615. A slide plate 625 is also provided and will be discussed below. The applier mechanism components further include a ratcheting pusher 627 slidably disposed on slide plate 625, a rocker pusher 629 having two support pins 633 for mating and allowing free rotation with corresponding supports 631 in the base 603 and cover 601, and a first pin 630, for engaging with the closer 611. A second pin 635 as well as a third pin 636 can also be provided on rocker pusher 629 for engaging with the transfer lever 615 and slide plate 625. A compression spring 637 can be used for storing energy when a clip is compressed and can be mounted on a compression spring support 639.

A linear, reciprocating motion with respect to the stationary base 603 and cover 601 is achieved for the closer 611 and transfer lever 615 for each cycle of the operating lever 207.

The clip applicator fork 609 has two jaws 649 preferably positioned at a downward angle with respect to the base 603 and a fork spring 641 which can have integral mounting holes 643. Mounting holes 643 engage with corresponding pins 645 located in base 603 to prevent applicator fork 609 from moving with respect to base 603. Fork spring 641 also preferably has integral cams 647 near fork jaws 649. The compliance and flexibility of fork 609 allows jaws 649 to be closed during operation of the device through flexibility of spring 641, and also allows the jaws to return to an open position due to the resilience of spring 641.

Applicator jaw member 609 and jaws 649 slide into a sleeve 651 at a front or distal end of closer component 611 and can be fastened to base 603 using parts and holes as discussed above. The rear or proximal end of closer 611 includes a follower 653 that slidably mates with pin 630 of rocker 629. Follower 653 has two downwardly depending structures, each of which defines a slotted cam for interacting with pin 630 as described.

Transfer lever 615 is disposed on closer 611. Transfer lever 615 includes a clip pusher 617 that includes a clip pusher portion 655 and ramp 657 at a distal end and a slotted structure 659 at a proximal end having a slot that slidably mates with second pin 635 of rocker 629. Clip shelf 619 can be positioned on the second base shelf and is preferably held stationary. Slide plate 625 can be slidably disposed on the same shelf.

Figure 22:
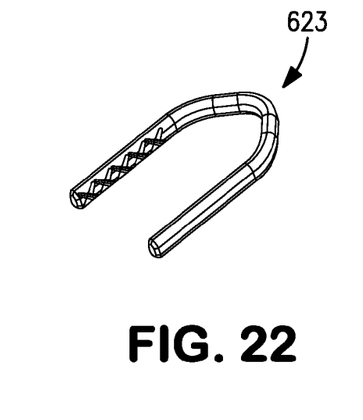
FIG. 22 shows a preferred clip for use with the present inventions.

Surgical clips 623 can be loaded serially onto clip shelf 619, with their open ends toward the cartridge front or distal end. Surgical clips 623 may be of any size and are generally U-shaped. A typical clip is as shown in FIG. 22. The number of clips per cartridge may vary depending on their size. Typically, 10 to 25 clips can be loaded into a cartridge. Clip shelf 619 and cover 601 form or define a supply channel for clips to progress distally toward the cartridge open end.

Ratcheting pusher 627 is positioned on top of the slide plate 625 and forms a clip advancing mechanism for advancing a line of clips along the clip supply channel. Ratcheting pusher 627 has a forked front end 683 conforming to a clip 623 closed-end contour for the purpose of pushing the line of clips so that a leading clip is in position to be pushed into fork jaws 649 by transfer lever 615. A plurality of teeth or ramps 661 on the underside of pusher 627 engage a plurality of tangs or spring biased ratchet pawls 663 located on the slide plate 625. Ramps 661 and pawls 663 are positioned in matching correspondence such that the length of one ramp 661 corresponds with one stroke of operating lever 207. Slide plate 625 advances the ratcheting pusher 627 the length of one surgical clip, preferably slightly further than such length, with each full operating stroke of lever 207. Slide plate 625 can be coupled to closer 611 for example by an additional slotted structure 613 which engages a pin on a rocker 629 such as pin 635, for example, or pin 636 where the stroke length of slide plate 625 may be the same as closer 611. Ratcheting pusher 627 and the slide plate 625 by their design and operation, and in cooperation with the transfer lever 611, regulate step-by-step or indexing movement of a line of clips through the clip supply channel toward the applicator jaws 649. The ratcheting pusher 627 is held against moving proximally with the slide plate by a pawl 628 which can be configured to engage with cartridge 105. Pawl 628 can be molded or otherwise provided on pusher 627. Further discussion of the clip feed mechanism is provided below.

Jaws 649 include spring biased arms 641 mounted with anchor pins 645 on base 603 with jaws 649 projecting from the front or distal end of the applicator at a downward angle. Sleeve 651 at the distal end of closer 611 is for closing these jaws, and then letting them open. This motion serves to clamp a clip positioned between jaws 649 onto a vessel or tissue as desired.

Jaws 649 are affixed to base 603 so that as closer 611 reciprocates, sleeve 651 rides along cam surfaces 647 of the fork jaws for causing the jaws to close a loaded clip, and for opening the jaws via spring compliance in arms 641 to receive another clip 623. The normal position for the closer 611 and jaws 649 occurs with the closer 611 at the rear or proximal end of linear excursion due to compression spring 637, with jaws 649 open and with closer sleeve 651 in an inactive position with respect to applicator jaws 649.

The interior of cover 601 can include upstanding sides above the second shelf to define the supply channel in conjunction with clip shelf 619. The supply channel is for receiving and retaining a line of clips 623. The clip channel has a stop defined by the shelf clip stop 621. This is further described and illustrated below.

Clip stop 621 formed on shelf 619 is defined by upwardly bent portions for engaging or blocking a leading clip at a shoulder or bale portion of the clip. Clip stop 621 has a "spring set" wherein the spring is normally positioned, or biased, at the surface of the shelf 619, and may deflect downward to allow a clip to pass.

Clip pusher 617 at the distal end of transfer lever 615 is mounted in this position with a "spring set" wherein clip pusher 617 is normally positioned, or biased, above the surface of transfer lever 615. Clip pusher 617 is accommodated in a slot in clip shelf 619 between clip stops 621.

Housing cover 601 may be transparent whereby a user can see the supply of clips through cover 601. Cover 601 may also have count marks indicating the number of clips remaining in the cartridge.

It is to be understood that closer 611 moves in a forward or distal linear excursion at the same time that transfer lever 615 moves in a proximal or rearward linear excursion due to the reciprocating action of the rocker pusher 629. The stroke lengths of these excursions need not be the same, and can be controlled by length and shape of rocker pusher 629. Rocker pusher 629 may be a first-class lever where the first pin 630 is for an input force, in this embodiment transmitted from handle 103 through closer 611 and through follower 653 to pin 630. The support pins 633 are the fulcrum and the second pin 635 is for the output force, transmitted through slotted structure 659 to transfer lever 615. The configuration of the rocker pusher 629 regulates the force applied to the transfer lever 615. This reciprocating linear motion serves to operate the clip applicator 105 by means of the closer 611. The closer 611 extends through the cartridge coupling end 605a, 605b where a forward force may be applied. In practice, cartridge 105 may be used with any suitable handle that provides a linear reciprocating motion.

Figure 8:
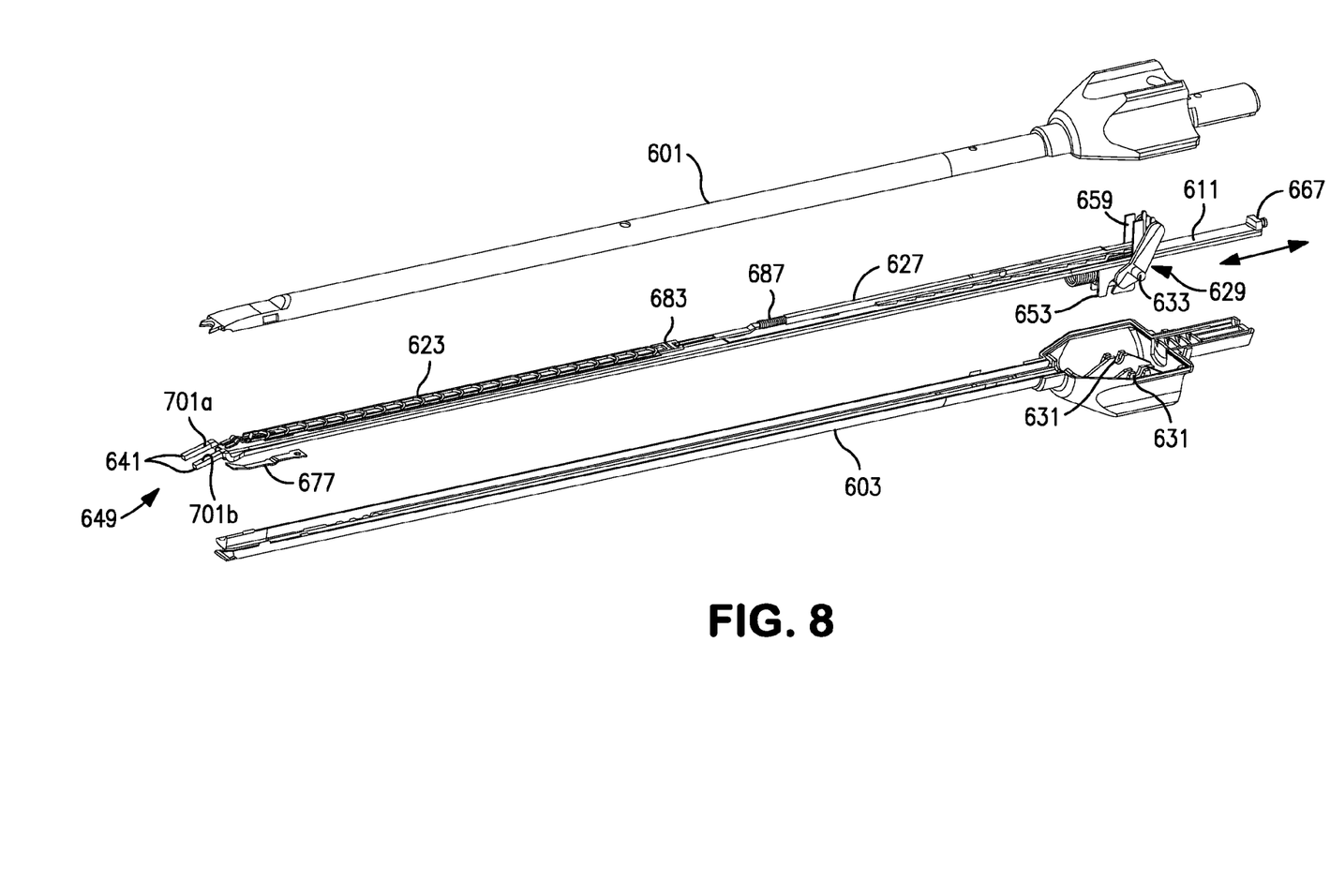
FIG. 8 is an exemplary perspective view of the cartridge with jaws open and the closer component at its most rearward travel.

FIG. 8 shows partially exploded components of cartridge 105 in a jaws-open and clip-loaded position with closer 611 in the most proximal or rearward position. The spring biased applicator jaws 649 with spring biased arms are able to move from open-to-closed-to-open positions in applying a clip. Inner surfaces 701a, 701b of the jaws are recessed to form cooperating channels for movement of the leading clip from the clip supply channel into the jaws. Outer surfaces of the jaws have aligned recesses defining cam surfaces cooperating with sleeve 651 of closer 611 for the purpose of closing the jaws during each forward excursion of closer 611. Jaws 649 are released to spring open on the rearward excursion of the closer 611.

Still referring to FIG. 8, cam surfaces 647 cooperate with sleeve 651 affixed to closer 611 for the purpose of closing the jaws during each forward excursion of closer component 611. Jaw arms 641 move from open-to-closed-to-open positions in applying a clip. The jaws are moved to a normally open position by means of the compression spring 637 which biases closer 611 proximally to allow jaws 649 to open. Forward inner surfaces 701a, 701b of the jaws can be recessed to form cooperating channels for holding each clip in the jaws as the jaws close.

The clip advance mechanism that includes clip pusher 627 and slide plate 625 act together for step-by-step or indexed movement of the clips 623 distally along the supply channel as desired and as described below.

Figure 9:
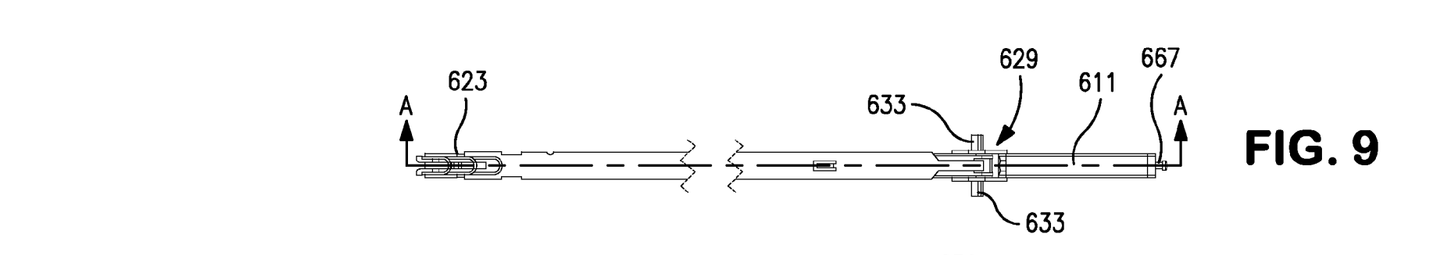
FIGS. 9-12 are is an enlarged views of components of the cartridge shown in FIG. 1.
Figures 10, 11, 12:
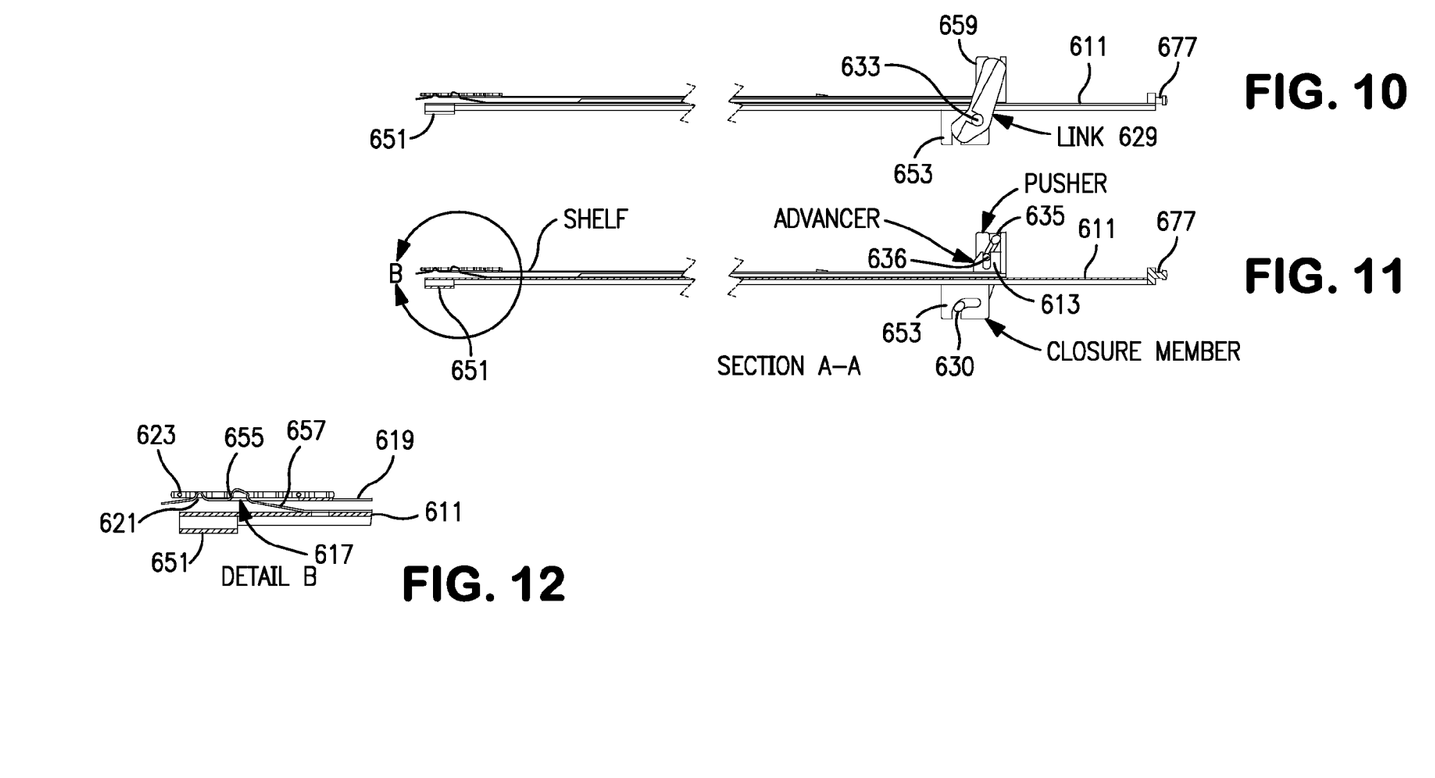
Figures 13, 14:
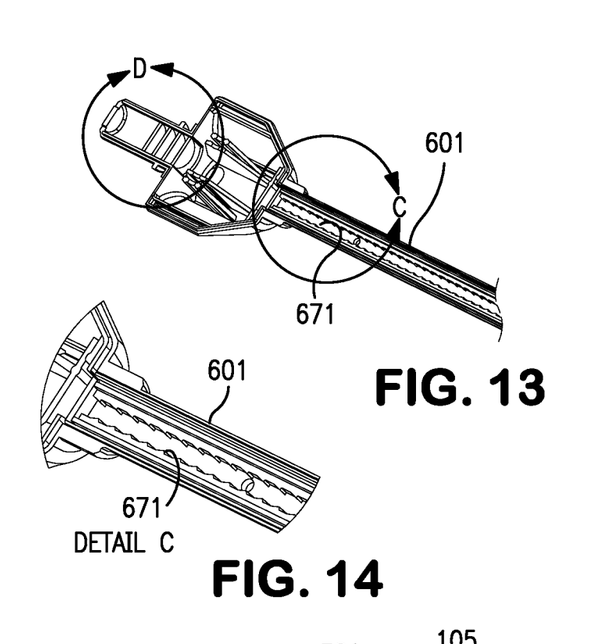
FIGS. 13-19 are enlarged views of components of the cartridge of FIG. 1 showing ratcheting pusher component and slide plate according to the invention.

Referring now to FIGS. 9-11, further illustrations and description are provided in connection with the reciprocating motion of various components within cartridge 105 when the applicator is operated. Handle 103 is operated to provide a translating force in this embodiment to a proximal end 667 of closer component 611. This force is signified in FIG. 8 by the double headed arrow shown in proximity to end 667.

Closing of the handle mechanism results in a distal movement of closer component 611 as illustrated by the arrow in this FIG. 11. In addition to moving sleeve 651 over the jaws to close them, this also moves follower 653 in a distal direction. Follower 653 is engaged with pin 630 of rocker pusher 629, and this results in pivot of rocker pusher 629 around support pin 633 in the direction illustrated by the arrow in FIG. 10. This results in a proximal movement of pins 635 and 636 as shown by arrow C. Pin 635 is engaged with slotted structure 659 which in turn is connected to transfer lever 615. Pin 636 is engaged with slotted structure 613 which in turn is connected to slide plate 625. Thus, the same distal motion of closer component 611 caused by the handle assembly also results in a proximal movement of transfer lever 615 along with attached clip pusher 617 and slide plate 625. When the handle reaches its fully closed position, the internal ratchet mechanism as discussed above releases and allows the handle of the device to be fully opened. This spring biased opening of the handles pulls closer component 611 back in a proximal direction, pivots rocker pusher 629 back around support pin 633, and thereby pushes transfer lever 615 and slide plate 625 in a distal direction. The respective movements remove sleeve 651 from jaws 649 and allow the jaws to return to an open position, while distal movement of transfer lever 615 engages clip pusher 617 with a leading clip 623 and pushes that leading clip into the jaws for application during the next closing stroke of the handles. Slide plate 625 simultaneously moves distally to advance the clips as desired. Thus, during the opening of the handles, movement of the components of FIGS. 9-12 is opposite to the direction shown by arrows in those figures.

FIG. 12 further illustrates the interaction of clip pusher 617 with a leading clip 623 and with clip stop 621 of clip shelf 619. FIG. 12 shows transfer lever 615 and connected clip pusher 617 in a proximal position with respect to clip shelf 619. This position corresponds to a fully closed position of the handle mechanism. In this position, it can be seen that clip pusher 617 is proximal of lead clip 623. As the handle mechanism is allowed to open, transfer lever 615 moves in a distal direction with respect to clip shelf 619 so as to position clip 623 distally into the jaws (not shown in these figures), where the clip is then ready for application during the subsequent closing stroke of the handles. As transfer lever 615 moves distally, the distal portion of transfer lever 615 including clip pusher 617 moves into the space between the distal prongs of clip shelf 619, so that clip pusher 617 can engage the proximally-facing bale of clip 623 and push clip 623 past clip stop 621 and into the jaws of the device. At the same time, slide plate 625 also moves distally and advances the clips 623 to fill the spot vacated by the lead clip as it is positioned into the jaws.

During subsequent closing of the handle mechanism, transfer lever 615 again moves proximally to prepare for loading the next lead clip in the jaws.

Referring now to FIGS. 13, 14, 16 and 17, components of the clip advancing mechanism are further illustrated. As indicated above, a stack of clips 623 (see also FIG. 7) is preferably advanced distally one clip at a time during operation of the applicator. This row of clips is advanced by ratcheting pusher 627, which contacts a proximal-most clip 623 with spaced distally extending members 683 (FIGS. 7, 9).

Figure 16:
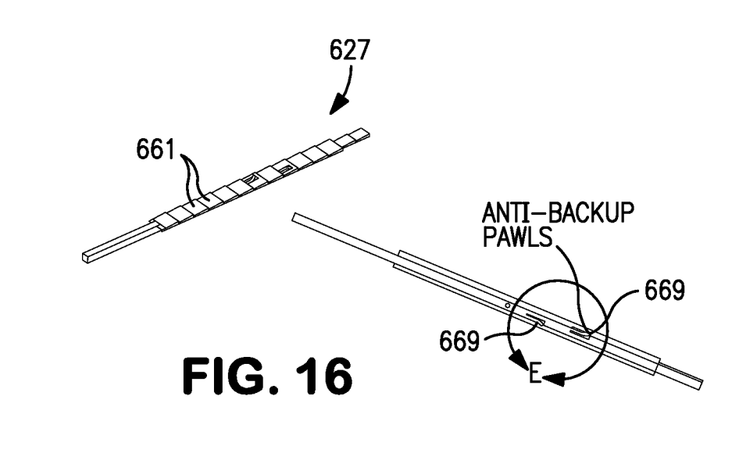
Figure 17:
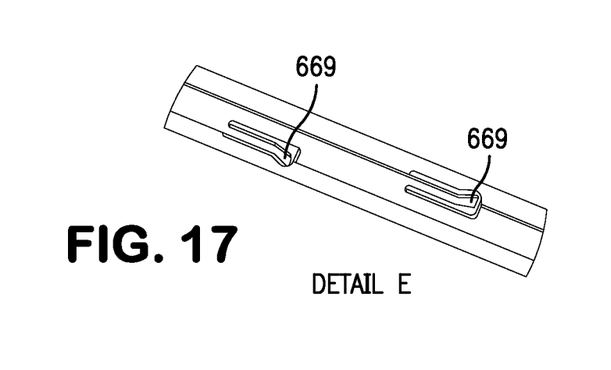

FIG. 16 further illustrates an enlarged portion of ratcheting pusher 627. As shown, ratcheting pusher 627 has a series of ramps 661 which are positioned and oriented to be engaged by pawls 663 of slide plate 625 (FIG. 7). Slide plate 625 is linked to rocker 629, and thus during each proximal movement of closer 611, slide plate 625 moves distally and caries ratcheting pusher 627 distally with it. During the return proximal motion of slide plate 625, pawls 663 slide proximally back past ramps 661 of pusher 627 in preparation for slide plate 625 to again engage ratcheting pusher 627 during the next distal stroke.

Ratcheting pusher 627 further has pawls 669 on an opposite side from ramps 661, and pawls 669 engage with ramp 671 (FIGS. 13, 14) on an inner surface of cover 601. Pawls 669 and ramp 671 engage in a lateral direction, and pawls 669 have lateral resilience so that they can snap past ramp 671 in a forward or distal motion of ratcheting pusher 627 with respect to cover 601. This prevents ratcheting pusher 627 from moving proximally during a proximal movement of slide plate 625 relative to cover 601. It should be noted that while these structures are shown as being laterally engaging, they could be engaged along vertically spaced surfaces, in similar fashion to the interaction between ramps 661 and pawls 663.

The advancing mechanism illustrated in FIGS. 13-14, 16-17 is particularly advantageous in that a serial distal movement of clips 623 is provided, in reliable and uniform fashion, without requiring any type of spring biasing of the stack of clips. This is advantageous as such springs typically have either too much force when the applicator is fully loaded, or too little force when the applicator is nearly empty.

Alternately, members 683 for pushing clips can be connected to pusher 627 through a post 685 which can be slidably received in pusher 627, with a spring 687 compressibly positioned between members 683 and pusher 627 to apply a holding force to clips 623 stored on shelf 619.

It should further be noted that members 683 of pusher 627 can advantageously be formed of aluminum. This provides for a more reliable lockout of the device when out of clips, as members 683 pass into the jaws at that point and prevent their closing. Further, in this embodiment, pusher 627 is a 3 piece assembly, which allows for end members 683 to be made from aluminum without requiring the rest of pusher 627 to be so made.

The operation of the applicator may be as follows. Cartridge cover 601 and base 603 are stationary with respect to movements of the component parts of the mechanism. At the beginning of an operating cycle, a cartridge 105 is coupled to handle 103 by inserting the coupling end into the quick release and twisting the cartridge until seated. The quick release locks the cartridge to the handle. When cartridge 105 is locked to handle 103, closer 611 (FIG. 8) contacts the front actuating surface 225 of carriage 217 (FIGS. 2 and 3). Cartridge 105 would not immediately be ready for use since a clip would need to be loaded in its jaws. Typically, the operating lever 207 would be in a fully extended position.

The clip applicator would need to be cycled once to load a clip. After initial loading, closer 611 may be at its most rearward travel position and transfer lever 615 at its most forward travel position. Closer 611 and actuating sleeve 651 are in an inactive position. As lever 207 and body grip 213 are squeezed, pawl 229 of carriage 217 engages rack 233 and permits only one way travel. Lever 207 cannot return to its beginning position until carriage 217 travels its full excursion.

Closer 611 moves in a forward or distal direction as the transfer lever 615 moves in a rearward or proximal direction. The travel sequence of each motion is critical and controlled by the location of pin 630, pin 633, pin 635, pin 636 and slots in slotted structures 653, 659 as well as configuration of closer 611 and transfer lever 615. Clip pusher 617 at the end of the transfer lever 615 descends below the clip 623 on clip shelf 619 as its ramp 657 makes contact with clip 623. Clip pusher 617 therefore in this proximal movement does not engage the end clip, especially through spring 685.

With closer 611 in a full forward, or jaws-closed position and with lever 207 fully depressed, the clip pusher 627 in this embodiment maintains close proximity to the last clip of the line of clips 623 and keeps the leading clip against clip stops 621 especially through spring 685.

With the operating lever 207 fully depressed, jaws 649 are compressed or closed (with no clip during the first cycle) and cam 231 of carriage 217 resets and allows operating lever 207 to extend or open. Compression spring 637 moves closer 611 rearward, while transfer lever 615 and slide plate 625 move forward. The forwardly moving pusher 617 of transfer lever 615 contacts a clip 623 on clip shelf 619 and catches the closed proximal end of the leading clip and pushes it into jaws 649. Pawls 663 of the forwardly moving slide plate 625 simultaneously catch clip pusher 627 thereby indexing forward by one step the relative position of clip pusher 627 and positioning a new lead clip for transfer into the jaws on the next cycle of transfer lever 615.

At an end of rearward excursion of carriage 217, cam 231 of carriage 217 sets and brings pawl 229 into contact with rack 233. Lever 207 is at its most outward position at this point. A new clip is loaded in position in the jaws and applicator 101 is ready for surgical application.

The clip is placed around an object (vessel or tissue). As operating lever 207 and body grip 213 are being squeezed, pawl 229 of the carriage 217 prohibits the jaws from opening and the clip from loosening. Closer component 611 moves in a forward or distal direction as the transfer lever moves in a rearward direction. The clip pusher 617 at the end of the transfer lever 615 descends below the plane of the clip 623 on clip shelf 619 as its ramp makes contact with the clip. At the maximum travel of lever 207, the clip is fully closed around the object, and cam 231 of carriage 217 resets and allows the jaws to relax along with lever 207.

As the lever 207 retracts to the fully open position, the reciprocating operation loads another clip into the applicator jaws as soon as they are fully open.

The invention provides that the clip applicator can be made as a disposable cartridge 105 to be inserted into a disposable or non-disposable handle 103 with cartridge 105 removed from the handle and discarded after its clips are consumed.

Figure 15:
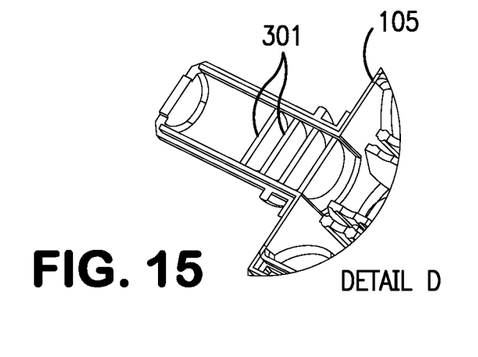

FIG. 15 shows an inside view of the proximal end of cartridge 105. In this view it can be seen that one or more grease dams 301 can be provided if desired, and these grease dams help to form a seal with components moving through the device. This advantageously helps to keep grease where it is desired, preventing it from migrating to other areas and allowing less to be used.

Figure 18:
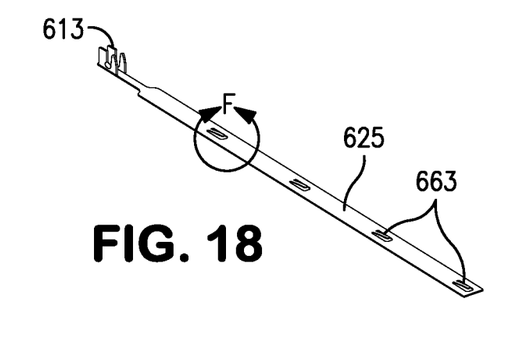
Figure 19:
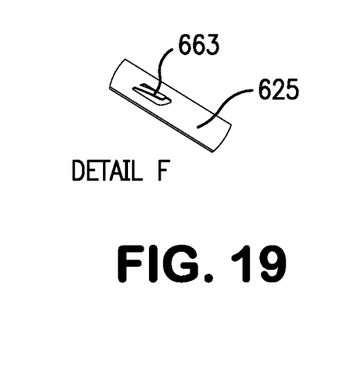

FIGS. 18 and 19 show additional detail of a slide plate 625 according to the invention. According to the invention, slide plate 625 receives translational movement during operation of handle 103, and translates longitudinally within cartridge 105. This movement of slide plate 625 serves to advance ratcheting pusher 627 as desired. Thus, during a distal movement of slide plate 625, pawls 663 engage ramps 661 of pusher 627 and move pusher 627 distally. This distal movement is set through design of the applicator to amount to the increment of the advance of one clip within cartridge 105. Proximal movement of slide plate 625 slides past pusher 627 without moving pusher 627, due to the anti-backup structure which holds pusher 627 through contact with the cartridge against proximal movement. Pawls 663 slide over ramps 661 during proximal movement of slide plate 625 into position to again move pusher 627 distally during the next distal movement of slide plate 625.

As shown, slide plate 625 has slotted structure 613 defining a slot for receiving a pin or other structure from rocker 629, preferably pin 636, so that movement of rocker 629 is translated to slide plate 625 as desired.

Figure 20:
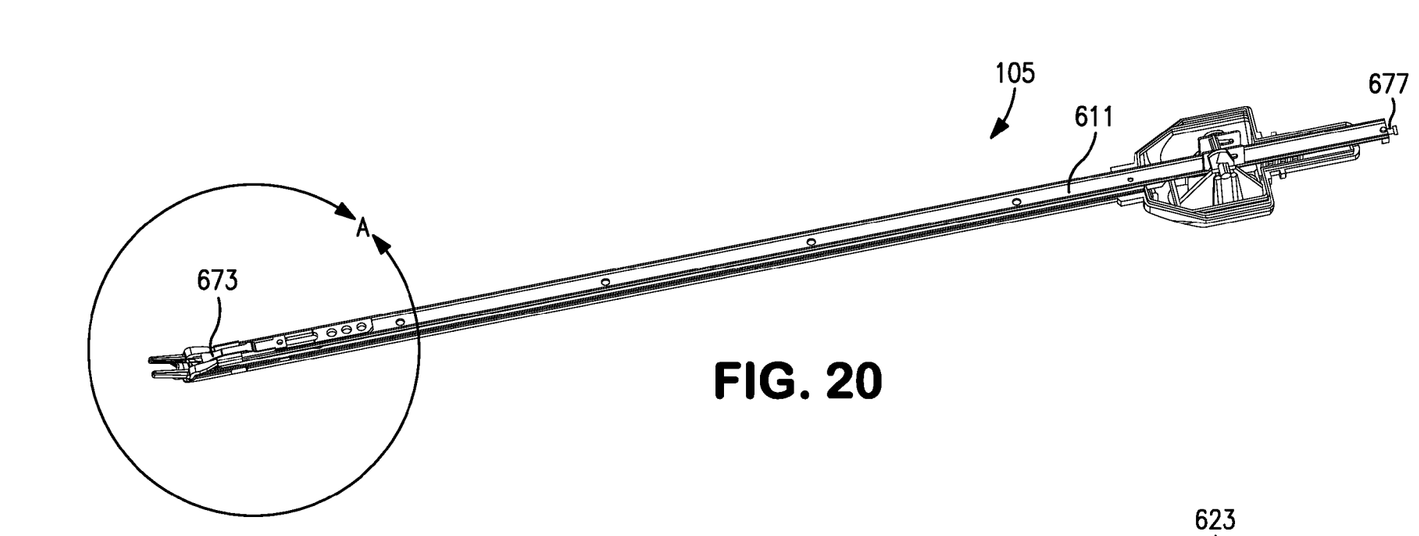
FIGS. 20 and 21 show a jaw blocker in accordance with an alternative embodiment of the present invention.
Figure 21:
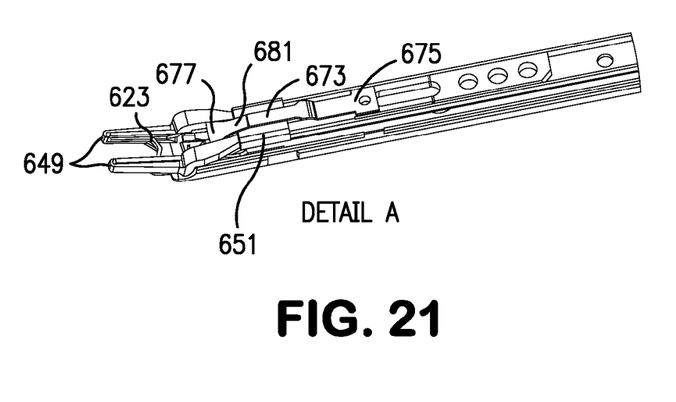

FIGS. 20 and 21 show an underside of the distal end of the applicator and illustrate a jaw blocker 673 which serves to keep jaws 649 in an open position. Jaw blocker 673 in this configuration is mounted to cartridge 105 in a fixed axial position with respect to jaws 649, and is a deflectable spring in similar fashion to other components of the apparatus. Jaw blocker 673 is preferably fixedly mounted to components of cartridge 105 at a proximal end 675 while a distal end 677 is configured to fit between jaws 649 when jaws 649 are in an open position.

In this configuration, jaw blocker 673 is advantageously positioned to interact with sleeve 651 of closer components 611. Interaction between sleeve 651 and a ramp portion 681 deflects distal end 677 between a blocking position wherein end 677 is positioned between jaws 649 and prevents their closing, and a clip applying position wherein distal end 677 is deflected downwardly by sleeve 651 to be out of alignment with jaws 649 so that jaws 649 can close and apply a clip as desired.

When sleeve 651 is in a proximal position, distal end 677 of jaw blocker 673 is between jaws 649. When sleeve 651 moves distally (as in during a clip closing procedure) sleeve 651 contacts ramp 681 and deflects jaw blocker 673 and end 677 out of alignment with jaws 649 to allow jaws 649 to close.

This feature will prevent a clip in the jaws from being dropped if the jaws are inadvertently moved inward. An example would be removing the device through a cannula and reinserting, which could otherwise dislodge a clip from the jaws.

With this embodiment, it is contemplated that applicator 101 could be shipped with the jaws.

Figure 23:
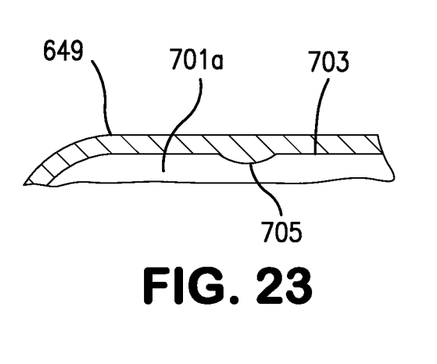
FIG. 23 is an enlarged cross-section taken through a jaw of the applicator according to the invention to show a modification of the inner surface of the jaw according to one aspect of the invention.

Referring to FIG. 23, another aspect of the invention is illustrated. FIG. 23 shows a cross section taken through a portion of a jaw member 649 and shows a channel 701a on an inner surface 703 of jaw member 649. Inner surface 703 is inwardly directed toward an opposing surface 703 of the opposite jaw (not shown in FIG. 23) and engages a clip to be applied. According to the invention, a protrusion 705 can be provided on inner surface 703, extending from inner surface 703 toward the opposing jaw. Protrusion 705 serves to act against a clip being closed as a "high spot" which makes for good closure of the clip, forming only a small "eye" in the bale portion of the closed clip, and closing the rest of the clip securely as desired without the legs spreading.

It should be appreciated that FIG. 23 shows protrusion 705 in an exaggerated size for the sake of understanding, and the actual size of the protrusion would be much smaller, preferably sufficient only to define a high spot of additional pressure on the clip being closed as desired.

Figure 24:
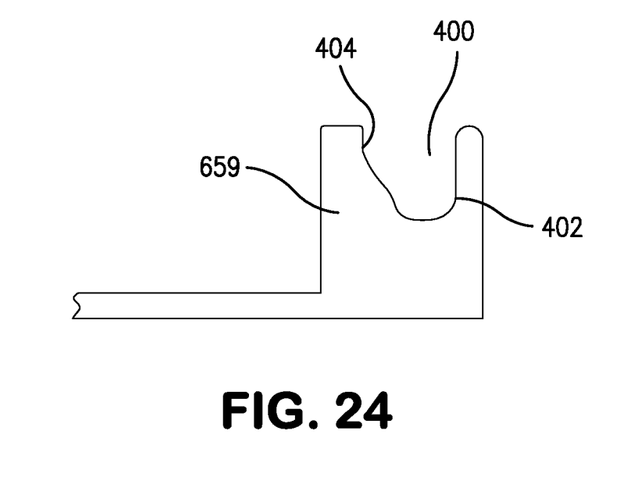
FIG. 24 shows an enlarged portion with additional detail of the slotted structure of the transfer lever according to the invention.

Returning to FIG. 7, slotted structure 659 is shown as two spaced upstanding structures having upwardly opening parallel slots 400 formed therein. Referring also to FIG. 24, an enlarged portion of slotted structure 659 is provided to show additional advantageous detail. As shown, slots 400 may have a narrower width at a base portion 402 of slot 400, and a wider width at an upper portion 404. The wider width 404 creates a lost motion with respect to pin 635 which advantageously allows jaws 649 to open before a clip 623 is advanced by movement of transfer lever 615. Thus, during a proximal movement of closer 611, which is engaged without lost motion via slotted structure 653 and pin 630, sleeve 651 immediately moves proximally to allow jaws 649 to open. Pin 630 therefore moves and begins to pivot rocker 629 around pin 633. This moves pin 635 distally within slot 400, but the extra width at the upper portion 404 allows the pin to move without starting the distal stroke of transfer lever 615 until pin 635 reaches the distal wall of slot 400 at the wider portion 404. In this way, as mentioned above, the jaws are allowed to open before a new clip is fed to them.

The apparatus according to the invention may be manufactured from any suitable materials for surgical instruments, including metals and plastics as appropriate. In this regard, however, certain parts are preferably made from metals, especially the various ratcheting structures which may have a tendency to wear too soon when made from plastic.

One or more embodiments of the present invention have been described. Nevertheless, it will be understood that various modifications may be made without departing from the spirit and scope of the invention. Accordingly, other embodiments are within the scope of the invention.

What is claimed is:

1. A surgical clip applicator, comprising:
    a handle configured to produce translational movement;
    a cartridge containing a plurality of clips arranged in a row, the cartridge comprising;
    a jaw assembly for receiving and closing a clip;
    a jaw closing mechanism for closing the jaw assembly;
    a clip feed mechanism for serially feeding a lead clip from the row to the jaw assembly;
    a clip advance mechanism for advancing the row as the lead clip is fed to the jaws; and
    a rocker mechanism for translating translational movement from the handle to opposite translational movement of the jaw closing mechanism in one direction and the clip feed mechanism and clip advance mechanism in an opposite direction.

2. The apparatus of claim 1, wherein the rocker mechanism comprises a double lever pivotably mounted in the cartridge and having a first lever engaged with the jaw closing mechanism and a second lever engaged with at least one of the clip feed mechanism and the clip advance mechanism.

3. The apparatus of claim 2, wherein one of the jaw closing mechanism, clip feed mechanism and clip advance mechanism is directly linked to the handle for receiving the translational movement, and transmits the translational movement to the other two mechanisms through the rocker mechanism.

4. The apparatus of claim 1, wherein each of the jaw closing mechanism, the clip feed mechanism and the clip advance mechanism is slidably disposed in the cartridge and has a slot interacting with a pin on the rocker mechanism.

5. The apparatus of claim 1, wherein the jaw closing mechanism comprises a sleeve sized to cooperate with an outer contour of the jaw assembly such that translation of the sleeve relative to the jaw assembly opens and closes the jaws.

6. The apparatus of claim 1, wherein the clip feed mechanism comprises a resilient member slidably positioned beneath the row of clips so that distal movement of the resilient member moves the lead clip of the row into the jaw assembly, and proximal movement of the resilient member positions the resilient member proximal of a next distal most clip in the row.

7. The apparatus of claim 6, wherein the resilient member has a substantially traverse distal surface for contacting a clip to be fed to the jaw assembly, and a sloped proximal surface for guiding the resilient member past a clip during proximal movement of the resilient member.

8. The apparatus of claim 1, wherein the clip advance mechanism comprises a slide plate and a ratcheting pusher, wherein the slide plate receives translational movement from the handle and transmits distal movement to the ratcheting pusher, and wherein the ratcheting pusher further comprises a pawl structure for engaging the cartridge against proximal movement whereby proximal movement of the slide plate does not result in proximal movement of the ratcheting pusher.

9. The apparatus of claim 8, wherein the ratcheting pusher comprises a first component engaged for distal ratcheting by the slide plate and second component disposed against a proximal most clip of the row, and further comprising a spring exerting a biasing force between the first component and the second component.

10. The apparatus of claim 1, wherein the jaw assembly comprises a pair of jaws having inwardly directed clip engaging surfaces, and further comprising a protrusion extending from at least one surface toward the other whereby proper closing of a clip is produced.

* * * * *